(12) United States Patent
Kost (10) Patent No.: US 6,866,644 B1
(45) Date of Patent: Mar. 15, 2005

(54) MYOTHERAPY MASSAGE DEVICE

(76) Inventor: Jonathan Kost, 9 Langley Park, Farmington, CT (US) 06032

( * ) Notice: Subject to any disclaimer, the term of this patent is extended or adjusted under 35 U.S.C. 154(b) by 120 days.

(21) Appl. No.: 10/056,772

(22) Filed: Jan. 23, 2002

(51) Int. Cl.⁷ .......................... A61H 1/00; A61H 23/02
(52) U.S. Cl. ............................ 601/49; 601/70; 601/90
(58) Field of Search ............................ 601/46, 49, 56, 601/57, 58, 70, 79, 98, 99, 100, 101–111, 67, 69

(56) References Cited

U.S. PATENT DOCUMENTS

| | | | |
|---|---|---|---|
| 3,310,050 A | * | 3/1967 | Goldfarb ...................... 601/79 |
| 3,710,785 A | | 1/1973 | Hilger |
| 3,841,321 A | | 10/1974 | Albach et al. |
| 3,854,474 A | | 12/1974 | Carruth |
| 4,343,303 A | * | 8/1982 | Williams ...................... 601/46 |
| 4,604,993 A | | 8/1986 | Moriwaki et al. |
| 4,632,095 A | | 12/1986 | Libin |
| 4,722,326 A | | 2/1988 | Ruderian |
| 4,732,140 A | | 3/1988 | Stoffregen |
| 4,850,340 A | | 7/1989 | Onishi |
| 4,984,568 A | | 1/1991 | Persuad |
| 5,020,517 A | | 6/1991 | Foster, Jr. et al. |
| 5,113,852 A | * | 5/1992 | Murtonen ...................... 601/47 |
| 5,179,940 A | | 1/1993 | Barreiro |
| 5,183,034 A | * | 2/1993 | Yamasaki et al. ............. 601/70 |
| 5,188,096 A | | 2/1993 | Yoo |
| 5,503,618 A | | 4/1996 | Rey |
| 5,542,907 A | * | 8/1996 | Chou .......................... 601/46 |
| 5,551,949 A | | 9/1996 | Kim |
| 5,582,582 A | | 12/1996 | Chapman |
| 5,611,771 A | * | 3/1997 | Taylor ......................... 601/70 |
| 6,511,446 B1 | * | 1/2003 | Wu ............................. 601/70 |

FOREIGN PATENT DOCUMENTS

| | | | | |
|---|---|---|---|---|
| JP | 409149924 A | * | 6/1997 | ............ A61H/7/00 |
| JP | 410094576 A | * | 4/1998 | .......... A61H/23/02 |

* cited by examiner

*Primary Examiner*—Justine R. Yu
*Assistant Examiner*—Quang D. Thanh
(74) *Attorney, Agent, or Firm*—McCormick, Paulding & Huber LLP (57) ABSTRACT

A myotherapy message device for the treatment of lower back myofosical pains having two laterally spaced massage heads each having a vibrator, and optionally a heater, disposed in the massage head, an apparatus for positioning the message heads vertically and laterally permitting a user to lay upon the device for relief of myofascial pains. A method for relieving myofascial pains involves contacting the affected muscles with the two laterally spaced massage heads and applying pressure, vibration and optionally heat to the areas of contact thereby relieving tension in the muscles.

23 Claims, 7 Drawing Sheets

MYOTHERAPY MASSAGE DEVICE

FIELD OF THE INVENTION

The present invention relates to a massaging device for alleviating lower back myofascial pains, and in particular to a massaging device having at least one protruding massage head to apply pressure, vibration and optionally heat to a focal region of the lower back.

BACKGROUND OF THE INVENTION

Myofascial pains are one of the most common causes of lower back pains. The two most commonly affected lower back muscles are the quadratus lumborum and lumbar paravertebral muscles. Conventional devices used to relieve lower back muscle pains frequently have a vibrating surface or roller surface which makes contact with the lower back region.

Previous devices have not been designed for use with a myotherapy treatment technique. Myotherapy is the treatment of muscle spasms through focally applied pressure to myofascial regions of pain (small bands of muscle spasms). The treatment involves a gradual increase in the applied pressure to release the spasm. The technique has been used for some time to manually treat lower back pain. Massage devices designed for myotherapy treatment are not known.

Massage devices which are worn like a belt to provide general, but not focused, massaging action are known. For example, U.S. Pat. No. 4,850,340 discloses a device for applying heat and vibration to the body by generating a magnetic field to relieve pain and stiffness, which device has individual hollow cases pivotally coupled together in a stand of cases, the ends of which are coupled to belt portions adapted to be attached together to support the strand around a body member. Similarly, U.S. Pat. No. 4,732,140 describes a vibratory massage device which has several belts of varying sizes, to which one or two vibrator units can be releasably attached for use on various body parts. These devices do not apply focussed pressure to the body areas to be treated.

Massaging devices for applying massaging action against the lower back by lying against the device are also known in the prior art. Typically, such devices are pad- or pillow-like and apply general massaging action to the body lying or siting on the device, as shown in U.S. Pat. No. 3,854,474 (padding material having massaging mechanisms thereunder), U.S. Pat. No. 5,020,517 (back massager attached to a back cushion), U.S. Pat. No. 5,503,618 (hydromassage pillow using heated jet pulsed water in a hollow pillow cushion), and U.S. Pat. No. 5,188,096 (massage apparatus which includes a mat that slips over the back of a seat). These devices, however, are not adjustable to apply focused massaging action as desired by the operator of the device.

Conversely, U.S. Pat. No. 5,179,940 ('940) describes a method for applying a mechanical massage which, while the back of a user is against the back rest of a chair or lying on a bed, uses a massage mechanism device having a pair of spaced parallel arm members and a massaging wheel rotatably supported on one end of each of the arm members. Although the device of patent '940 allows adjustment of the distance between each arm member, it does not permit focused massage utilizing heat or vibration.

U.S. Pat. No. 5,582,582 ('582) discloses a device having a massaging mechanism with a plurality of rotatable heads with projections which can be positioned upon the user's back for applying massaging action thereto. The user lies upon their stomach while the massaging mechanism is positioned to apply massage therapy to the user's back. The device of the '582 patent has a frame with legs that permit positioning the frame on top of a massage table/bed. U.S. Pat. No. 4,984,568 likewise shows a back massaging device for use on a bed to apply massage therapy to the back while the user is on their stomach, which device has a clamp for securing to a bed frame and an arm for positioning the massaging device. Neither of these devises permits the user to lie on his back and adjust the pressure. Each of these prior devices requires a second person to operate and position the device correctly.

Handheld massaging devices are also well known. U.S. Pat. No. 4,632,095 shows a pressure-point attachment for use with electrical hand-held massagers to apply point-pressure combined with vibration to known body pressure points. U.S. Pat. No. 3,841,321 discloses a therapeutic massage unit having an enclosed casing with cylindrical body wall and hemispherical end wall, and a handle for manually applying massage to the body.

Massage devices which apply heat and vibration are known in the prior art. For example, U.S. Pat. No. 4,722,326 describes a vibratory therapeutic device which has a plurality of interchangeable massage heads, wherein only one massage head may be used at a time and heated air flow may be applied through the head. U.S. Pat. No. 5,551,949 describes an infrared massage device which has a hand-held housing, a mechanical vibration generator disposed within the housing, mechanical vibration being transmitted to at least a heat-conductive portion of the housing, and at least one source of infrared radiation. U.S. Pat. No. 4,604,993 discloses a hand-held vibratory massage device with a heating element having an applicator head which can apply both tapping and rubbing action. U.S. Pat. No. 3,710,785 shows a hand-held massager device used to apply vibration and infrared heat to the body, which massager includes a floating head connected to the main housing of the massager by a coil compression spring.

Handheld devices do not permit the user to apply pressure to their own backs. Such devices require a second person to apply the pressure. Also, the pressure applied manually by a second person does not permit the user to finely adjust the pressure applied but instead requires the user to give the second person verbal instructions which may or may not be understood and followed. Furthermore, prior art devices, which a user lies upon, do not permit focused application of pressure, massaging action, or heat, but instead provide generalized massaging action or heat.

None of the above inventions and patents, taken either singularly or in combination, is seen to describe or suggest the instant invention as claimed. Thus, a massaging device to alleviate lower back myofascial pain solving the aforementioned problems is desired.

SUMMARY OF THE INVENTION

An object of the present invention is to provide directed focal pressure to lower back muscles. Previous devices have not isolated specific lower back muscles for treatment and have not implemented a myotherapy modality of treatment (graduated slight increases in applied focal pressure) using ones own body weight to apply the necessary pressure for the treatment.

Another object of the present invention is to provide vibratory massage action to a focal region of the lower back muscles. Previous devices have typically used generalized massage action to the back or require an individual other than the user to operate the device. The present invention permits the user to direct focalized massage action to the back as desired without the further assistance of an additional person.

Yet another object of the present invention is to provide heated focal pressure to lower back muscles. The device also possesses the option of using heat within the vibrating head for additional therapeutic benefit.

A further object of the present invention is to provide a method for using the device to alleviate myofascial pains of the lower back region. The device is designed to permit the user thereof to gradually increase pressure to the effected muscle regions as desired.

The present invention relates to a massaging device used to alleviate lower back myofascial pain. The device possesses at least one protruding massage head which applies vibration and heat with focal pressure to the lower back muscles affected by myofascial pains. Pressure is applied by the individual lying on the device. Each of the protruding components individually can be adjusted to provide the appropriate measure of vibration and, if desired, heat. The distance between massage heads and the height of each massage head are also adjustable to accommodate individual anatomical variation and to apply optimal focal pressure to the affected lower back musculature. Vibration frequency is maintained from about 90 Hz to about 110 Hz range to optimize the pain reducing benefit. Typically, a vibration frequency of about 100 Hz releases the spasms and pain in the lower back when applied thereto for a short time.

Previous devices were not specifically designed to isolate treatment to these specific lower back muscles. These devices do not employ a gradually increased application of pressure (myotherapy) to release the spasm. They also do not use the individuals own body weight as a means of applying the needed pressure. The present device is used in such a way that the individual simply lies on top of it, with the device applying pressure to the problematic musculature. Lying down enables the lower back musculature a greater degree of relaxation because the lower back muscles are not being used to maintain posture. Relaxed muscles are preferable for optimal therapeutic benefit.

The therapeutic device possesses two spaced substantially parallel vibrating massage heads each of which applies pressure to the specific right and left-sided lower back muscles (quadtratus lumborum and lumbar paravertebral muscles) desired. The device may be used unilaterally or bilaterally. Adjusting the distance between the vibrating heads allows for anatomical individual variability when making contact with the right and left side lower back muscles. The device may be used unilaterally by further increasing the distance between the heads. With the individual lying on the device focal pressure is applied to the spastic region in the muscle. The individual being treated self adjusts a knob or crank provided on the device that finely alters the elevation of the heads. Increased elevation results in increased applied pressure to the spastic region of the muscle (Myotherapy). The treatment may be only minutes in duration and results in a release in the band of muscle spasticity thereby reducing myofascial pain.

An additional therapeutic benefit is obtained due to the vibrational effect of the heads. The frequency of the vibration is controlled by a knob on the power source box. The individual may self-regulate the frequency of the vibration based upon comfort level. The device possesses a range of applied vibration frequency which includes vibrational frequencies from about 90 Hz to about 110 Hz. As has been shown in the medical literature, reduction in pain is frequently seen at about 100 Hz. Further benefit is obtained by the option of providing applied heat to the focal region.

An advantage of the present invention is the ability for the individual to self-regulate the pressure. The knob or crank provided on the device permits the user to adjust and fine-tune the relative vertical height, and horizontal position, of the substantially parallel massage head(s) while in use.

Another advantage is that the device can be operated by the user alone and does not require a second person to help the user focus the treatment. An individual suffering from myocardial pain can treat themselves alone without assistance.

These and other objects and advantages of the present invention will become readily apparent upon further review of the following drawings and specification.

BRIEF DESCRIPTION OF THE DRAWINGS

The novel features of the described embodiments are specifically set forth in the appended claims; however, embodiments relating to the structure of the present invention may best be understood with reference to the following description and accompanying drawings.

FIG. 5b is a side view of the lift arm of FIG. 5a.

Similar reference characters denote corresponding features consistently throughout the attached drawings.

DETAILED DESCRIPTION OF PREFERRED EMBODIMENTS

Figure 1:
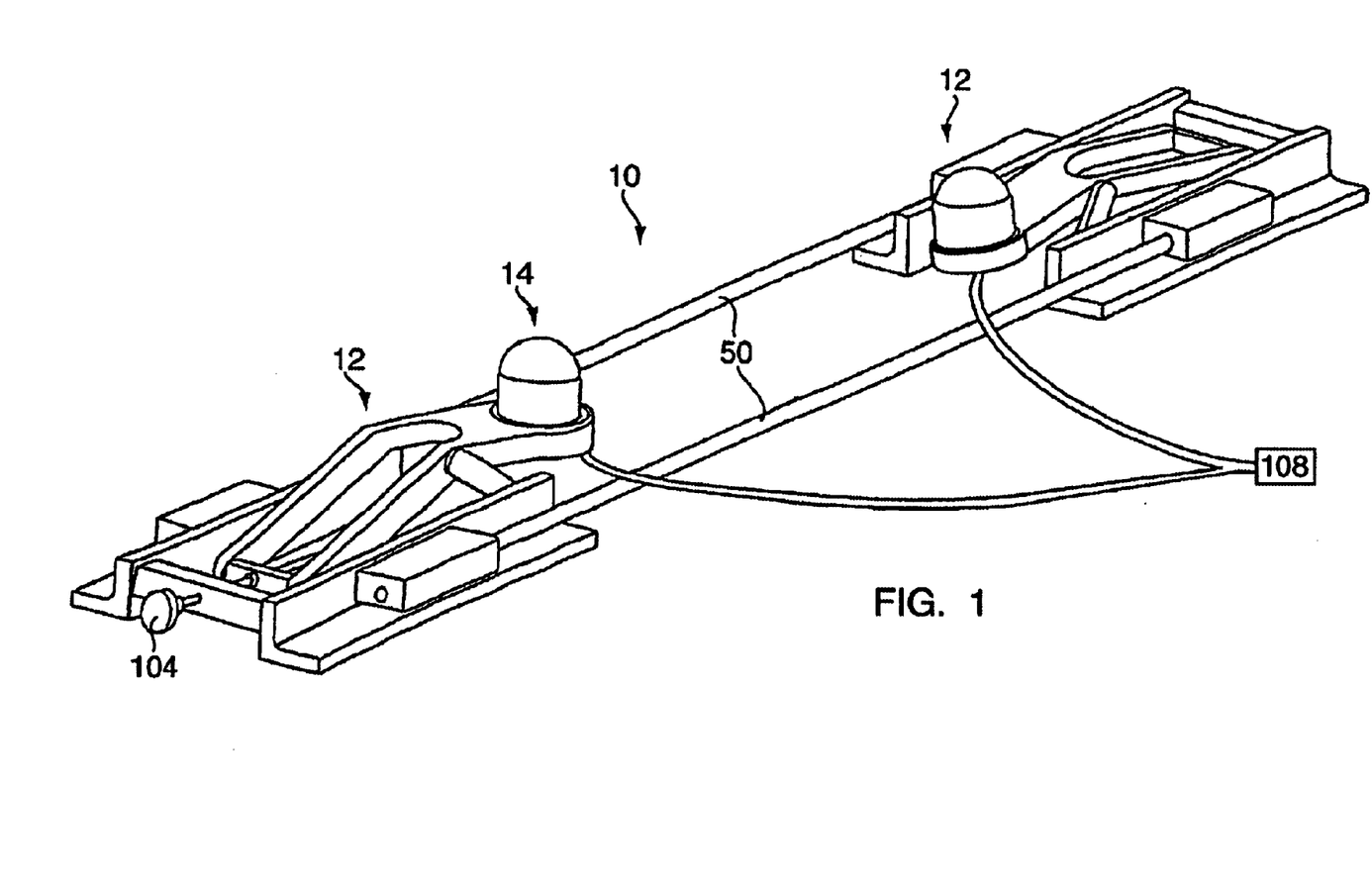
FIG. 1 is a schematic perspective view of an embodiment of the myotherapy massage device of the present invention consisting of two opposing massage devices.
Figure 2:
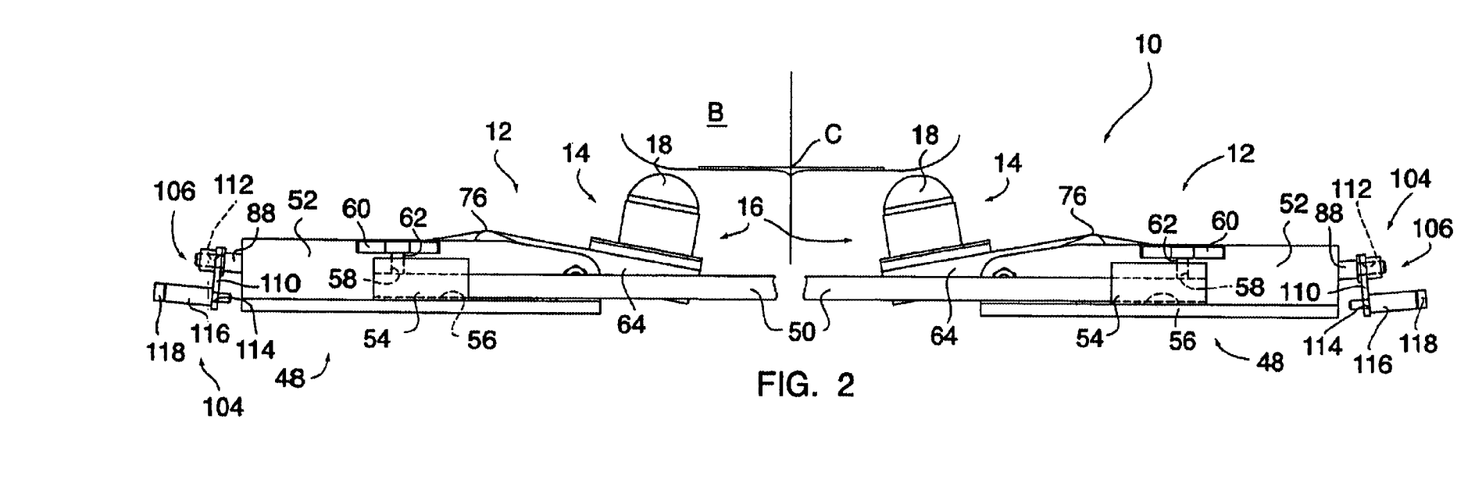
FIG. 2 is a side view of a myotherapy massage device according to the embodiment of FIG. 1 showing a schematic of a user's back and relative placement of the device.
Figure 3:
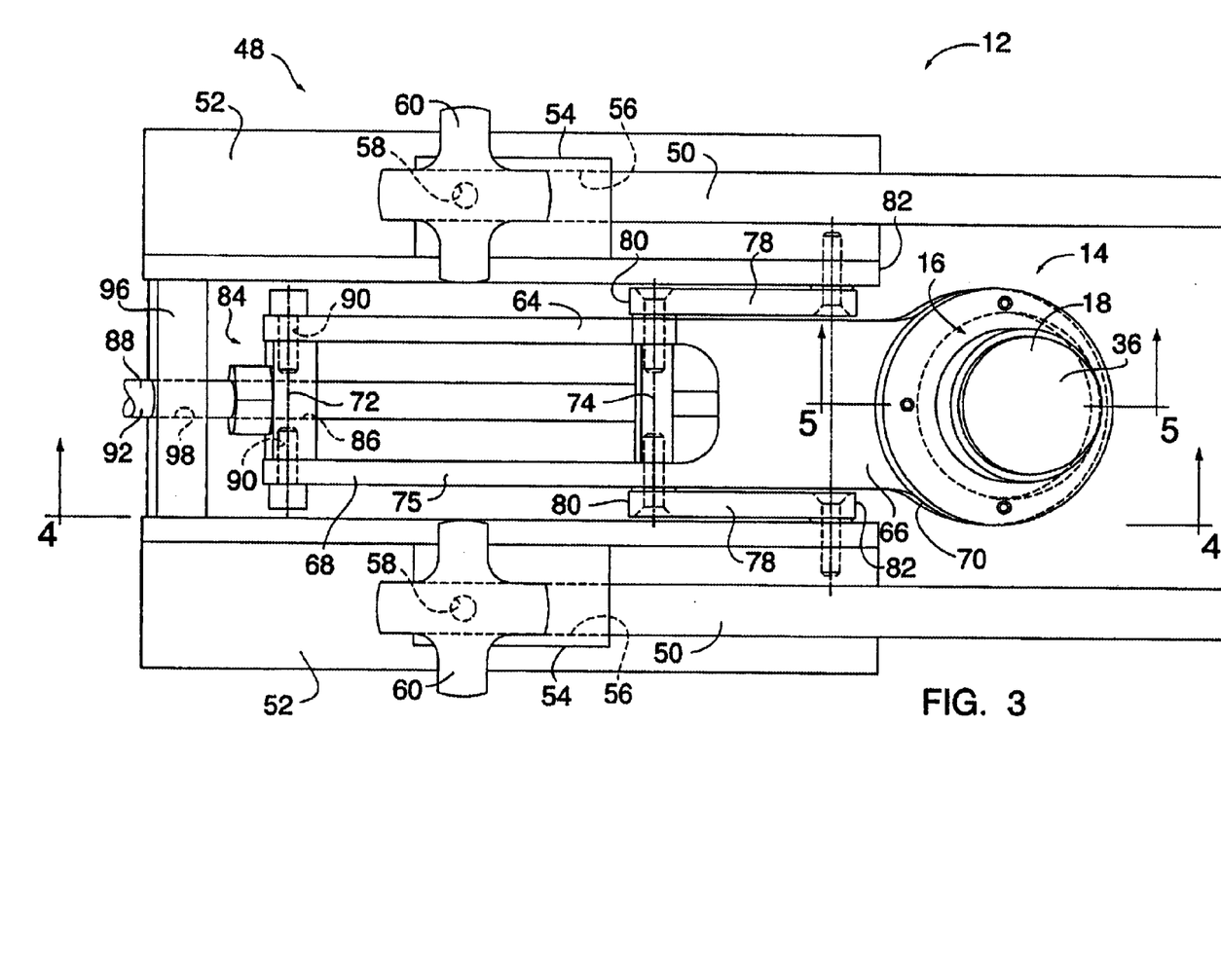
FIG. 3 is a top view of the massage device of the embodiment of FIG. 2.

A myotherapy massage device 10 for alleviating lower back myofascial pain, as shown in FIGS. 1 and 2, is contemplated by the present invention. The myotherapy massage device 10 possesses at least one massage device 12, as shown in FIG. 3, having a protruding massage head 14 that applies vibration with focal pressure to the lower back muscles affected by myofascial pains. The massage head 14 may also apply heat to the lower back muscles. The pressure is applied by the individual lying on the device. Each of the protruding components individually can be adjusted to provide the appropriate measure of vibration and heat, if available. The distance between massage heads and the height of each massage head is also adjustable to accommodate individual anatomical variation and to apply optimal focal pressure to the affected lower back musculature.

A method for treating lower back myofosical pains using the myotherapy massage device 10 of the present invention comprises effecting the release of muscle spasms [treatment] by gradually increasing pressure on a targeted focal area. The user lies upon the device so that their back B is in proper orientation with the center line C of the spinal column positioned roughly equidistant between the two massage heads, as shown in FIG. 2. The method for treating lower back pains according to the present invention is discussed hereinafter in greater detail.

Figure 6:
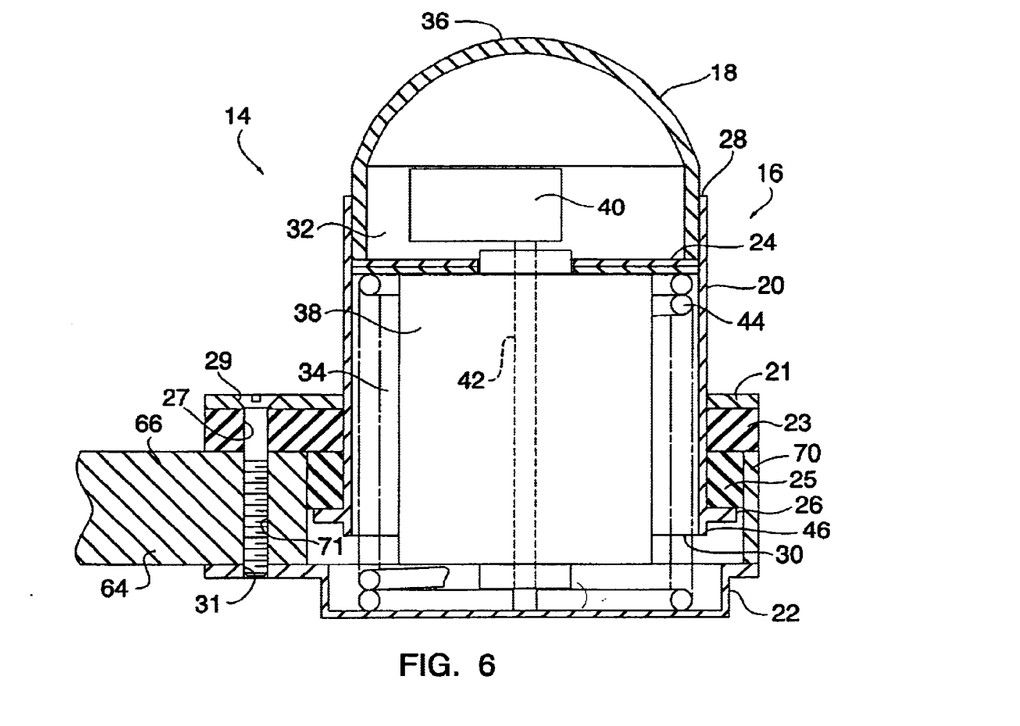
FIG. 6 is a secitional view taken along line 5—5 of FIG. 3.

The myotherapy massage device 10 for the treatment of lower back myofosical pains has two laterally spaced massage devices 12 each having a massage head 14. Each massage head 14 has a vibrator, as discussed hereinbelow. The myotherapy massage device 10 permits a user to position the massage heads 14 vertically and laterally. The massage heads 14 of the massage device 10 are laterally spaced so that the massage heads are substantially parallel to one another in order to contact a user's back in roughly the same region on both sides of the center line of the spinal column. Each massage head has a motor housing 16 enclosing the vibrator. The motor housing 16 has a tube 20, as shown in FIG. 6, having a bottom end 30 and a top end 28. A bottom cap 22 is disposed on the bottom end 30 of the tube 20. A top cap 18 is disposed on the top end 28 of the tube 20 opposite the bottom cap 22. The motor housing 16 may have an edge or protrusion, referred to herein as a lip 26, circumnavigating the tube 20 adjacent the bottom end 30 of the tube 20 such that some length 46 of tube extends therebelow. The phrase "laterally spaced" as used herein defines the substantially opposing but parallel positions of contact areas of the massage heads 14, and is not intended to imply that the massage heads 14 or the massage devices 12 are in fact positioned strictly parallel to one another. The term "contact area" refers to the area of contact between the massage head 14 and a user of the myotherapy massage device 10.

Note that the motor housing 16 need not be cylindrical as shown in the figures. The tube 20 may have a square, circular, oval, etc. cross section. Furthermore, the top cap 18 has a shape complementary to the tube 20 shape and need not be rounded but may present a flat surface having any cross sectional shape desired. In fact, the over all shape of the message head need not be restricted to the shape shown in the figures. Message heads of varying shapes, such as square, rectangular and the like, are also contemplated by the present invention. Furthermore, the top cap of the present invention may include interchangeable shapes/styles which will provide for a precise to a broad contact area as desired. Various shapes/styles may be desired to alter the amount of surface area applying pressure to the region of contact on the body.

A retention plate 24 may be disposed between the top and bottom ends 28 and 30 of the tube 20 such that the top cap 18 contacts and rests upon the retention plate 24. Top and bottom spaces 32 and 34 are created within the motor housing 16 by the retention plate 24. The top space 32 adjacent the top cap 18 is smaller than the bottom space 34 adjacent the bottom cap 22. The top cap 18 may have a convex top surface 36.

Figure 7:
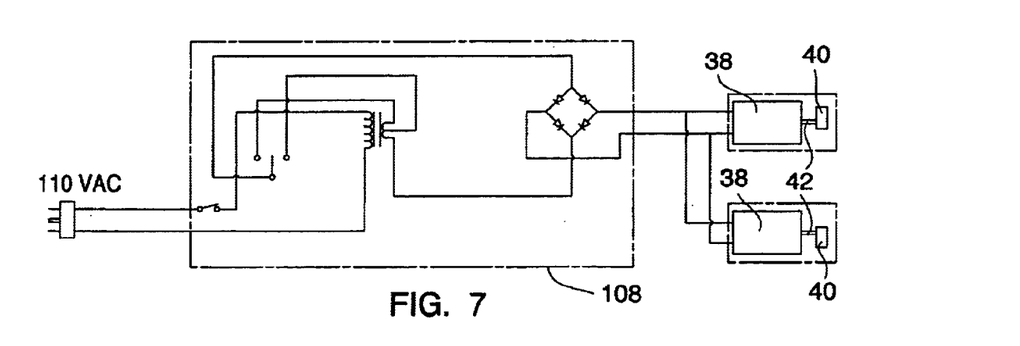
FIG. 7 is a schematic view of a control box and vibrator assemblies of the current invention.

The vibrator may have an electric powered motor 38 to produce vibration by turning an axle 42 with an asymmetric weight 40 attached thereto, as shown in FIGS. 6 and 7. The motor 38 may be disposed in the bottom space 34 and attached to the retention plate 24 so that the weight 40 is permitted free movement in the top space 32.

A heater may be disposed in the motor housing 16 to heat the top cap 18. The heater in the top cap 18 is taken from the group consisting of heating coils, infrared radiation, resistance wires, and resistance wire tape, all of which are well known in the industry. The heater may be disposed within the top cap 18 and in contact thereto for conducting heat therethrough. Furthermore, the top cap 18 may be composed of a heat conducting material.

A coil compression spring 44 may be disposed in the motor housing 16 between the bottom cap 22 and the top cap 18 thereby cushioning the vibrator so the vibration of the massage head 14 is dampened with respect to the motor housing 16, in general, and amplified with respect to the top cap 18, in particular. The coil compression spring 44 may be disposed in the motor housing 16 between the bottom cap 22 and the retention plate 24, as shown in FIG. 6, thereby cushioning the vibration such that the vibration of the massage head 16 is dampened with respect to the motor housing 16. In other words, the top cap 18 as it rests on the retention plate 24 is buoyed by the coil compression spring 44 such that the vibration generated by, for example, the rotating asymmetric weight 40, is concentrated in the top cap 18 and the retention plate 24 as the vibrator is attached thereto.

In one of the embodiments, the aspect of the massage device 12 for positioning the massage heads 14 laterally comprises two opposing base assemblies 48 slidably connected to one another by two guide rods 50. Each base assembly 48 is made up of two opposing bases 52, shown in FIG. 3, with the massage heads disposed between the bases, as shown in FIG. 1. A guide 54 is disposed on each base 52 having a first opening 56 therethrough for slidably receiving the guide rod 50, as shown in FIGS. 1, 2 and 3.

Each guide 54 may further comprise a perpendicular threaded second opening 58, bisecting the first opening 56, for receiving a knob 60 having a screw extension 62 thereon which can be tightened to secure the guide rod 50 in place. Other methods for restricting the movement of the base assemblies 48 relative to the guide rods 50 are also contemplated by the present invention.

Figure 4:
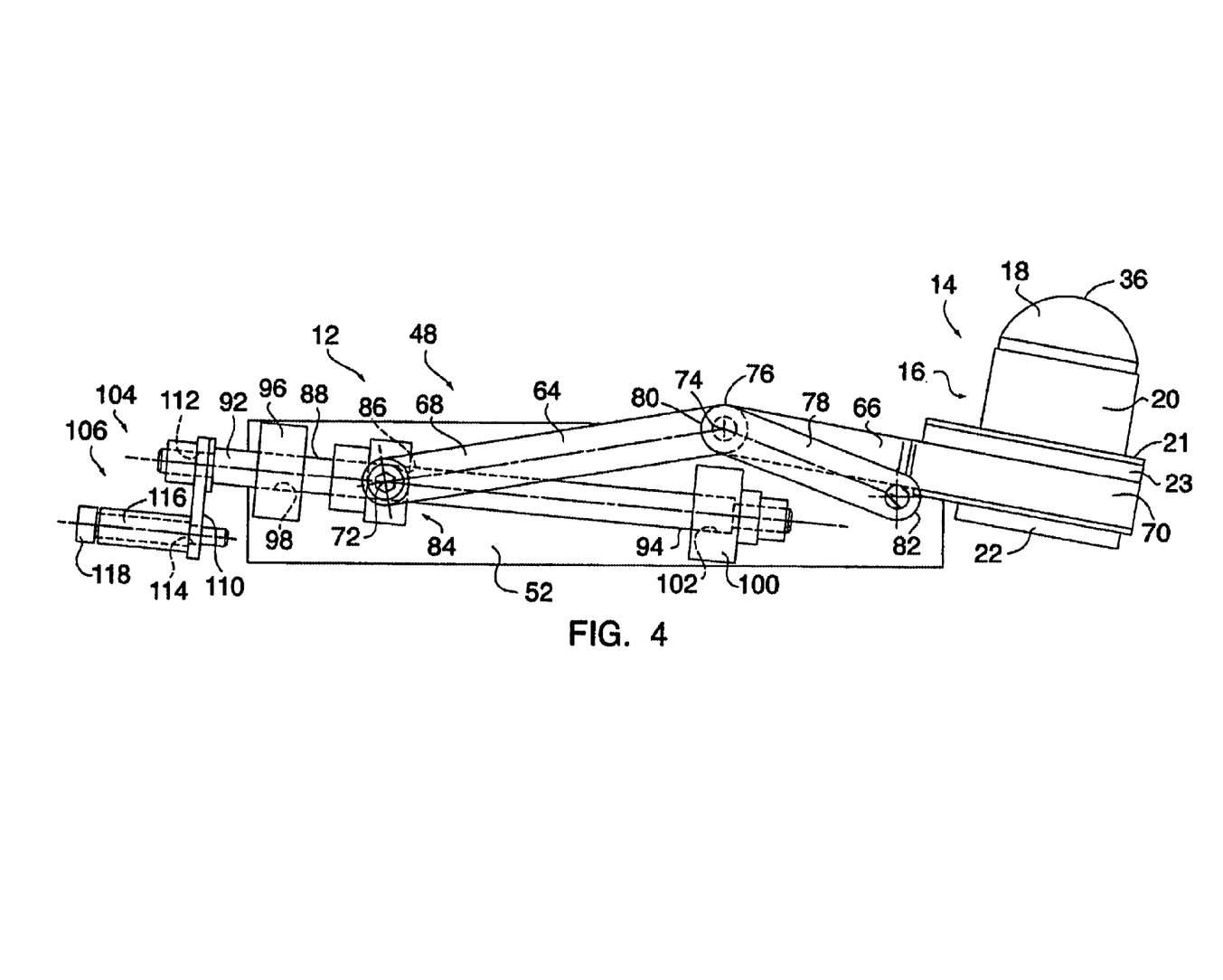
FIG. 4 is a sectional view taken along line 44 of FIG. 3.
Figure 5A:
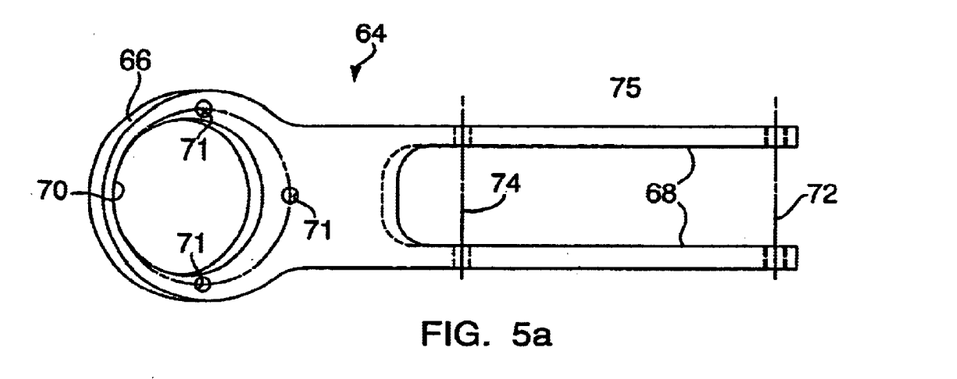
FIG. 5a is a top view of a lift arm used in the embodiment of FIG. 1.

The aspect of the invention used to position the massage heads 14 vertically utilize the same base assembly 48 as discussed above. The two opposing bases 52 have a lift arm 64 disposed between the two opposing bases 52, as shown in FIG. 4. The lift arm 64 has a length with a first and second end 66 and 68. A structure to attach the massage head 14 at the first end 66 is provided. The structure shown in FIGS. 4 and 5a is a ring structure 70 which receives the bottom end 30 of the massage head's 14 motor housing 16 therethrough. Other structures such as an open ring structure, or an indentation may be substituted for the ring structure 70. At the minimum, the massage head 14 may be fixed by any well-known means directly to the first end 66 of the lift arm 64 instead of a ring structure 70 or any other structure.

Figure 5B:
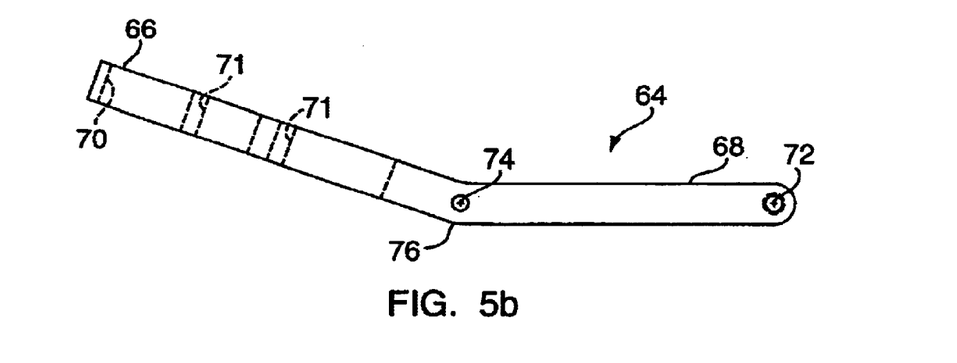

A specific example of a design for attaching the massage head 14 to the lift arm 64 is shown. The lift arm 64 has a ring structure 70 at the first end thereof. The ring structure 70 has threaded openings 71 for receiving screws. A gasket 23 and a plate 21 are provided which have openings 27 and 29 corresponding to the threaded openings 71 of the lift arm 64 which are shown in FIGS. 5a and 5b. The bottom cap 22 is also provided with corresponding threaded openings 31. A rubber gasket 25 may be disposed around the tube 20 of the motor housing 16 adjacent the lip 26. The massage head 14 is disposed on the ring structure 70 so that the bottom cap 22 is adjacent one side of the lift arm 64 while the gasket 23 and plate are disposed on the other side of the lift arm 64. The bottom end of the motor housing is disposed adjacent the bottom cap 18 and the lip 26 then the rubber gasket 25 is placed around the housing and adjacent the lip 26, the remaining gasket 23 and plate 21 are placed over the motor housing as shown. The threaded openings 71 and the corresponding openings 27, 29 and 31 are matched and screws or the like are inserted therethrough in order to secure the massage head in place.

A pivot axis 72 at the second end 68 of the lift arm, and a lift axis 74 disposed between the first and second ends 66 and 68 of the lift arm 64. The pivot and lift axes 72 and 74 may consist of openings with axles extending therethrough, or partially therethrough, provided in the lift arm 64, as shown in the FIGS. 4 and 5B. Alternatively, the pivot and/or lift axes 72 and 74 may consist of protrusions extending out from the lift arm 64 in a manner analogous to the axles shown, as is well known in the art. A bend 76 in the lift arm 64 may be provided at the point of the lift axis 74 so that the massage head 14 can be positioned correctly for use, as shown in FIG. 5b.

Two linkers 78 are provided to pivotably attach the lift arm 64 to the bases 52 as shown in FIG. 4. Each linker 78 has first and second ends 80 and 82, with the first end 80 of the linker pivotably disposed on the lift axis 72 and the second end 82 of the linker pivotably disposed between the two opposing bases 52. The two ends may have openings for receiving axles or protrusions therethrough. Alternatively, the linker may have protrusions therefrom for insertion into openings at the lift axis and/or in the bases 52.

A pivot axis assembly 84 has a first threaded opening 86 therein forming a passage for receiving a crank shaft 88 and a second opening 90 for receiving the pivot axis 72 of the second end 68 of the lift arm 64. Optionally, the second end of the lift arm may comprise a U-shaped extension 75 such that the pivot axis assembly fits between two legs of the U-shaped extension 75. The crankshaft 88 has a length, a first threaded end 92, and a second threaded end 94. A first spacer block 96 attached to and disposed between the two opposing bases 52 and having an opening 98 for rotatably receiving the first end 92 of the crank shaft 88 therethrough is provided. A second spacer block 100 attached to and disposed between the two opposing bases 52 and having a threaded opening 102 therein for receiving a second end 94 of the crank shaft 88 is also provided. The crankshaft 88 has a handle 104, a crank 106 or other such device for rotating the crankshaft 88 disposed on the first end 92 of the crankshaft 88. The crank 106 may consist of one piece. Alternatively, the crank may have a crank plate 110 with two openings wherein the first opening 112 is affixed to the first end 92 of the crank shaft 88 having a screw 118, or equivalent, through the second opening 114 thereof with a sleeve handle 116 slidably engaged on the screw 118.

A controller 108 for modulating the vibration frequency may be provided. FIG. 7 shows a possible configuration for the controller 108 and the electrical connections to and from the motors 38. The device may operate at a vibration frequency greater than about 90 Hz, and less than about 110 Hz to provide effective pain relief. A vibration frequency of about 100 Hz is desired.

Figure 8:
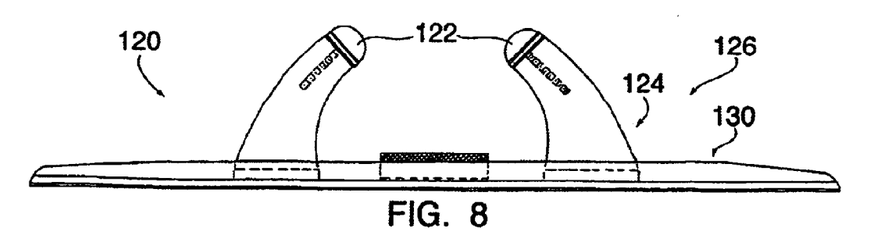
FIG. 8 is a schematic view of an alternate embodiment of a myotherapy massage device of the present invention.
Figure 9:
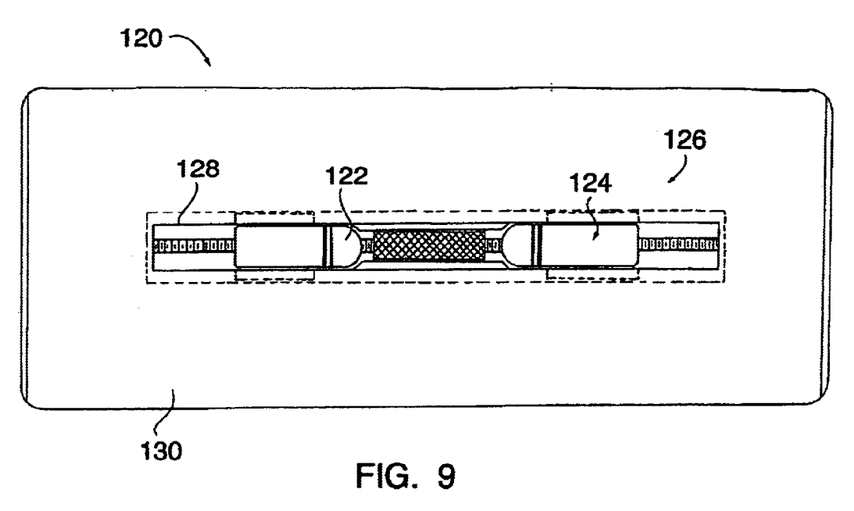
FIG. 9 is a schematic view of the embodiment depicted in FIG. 8.
Figure 10:
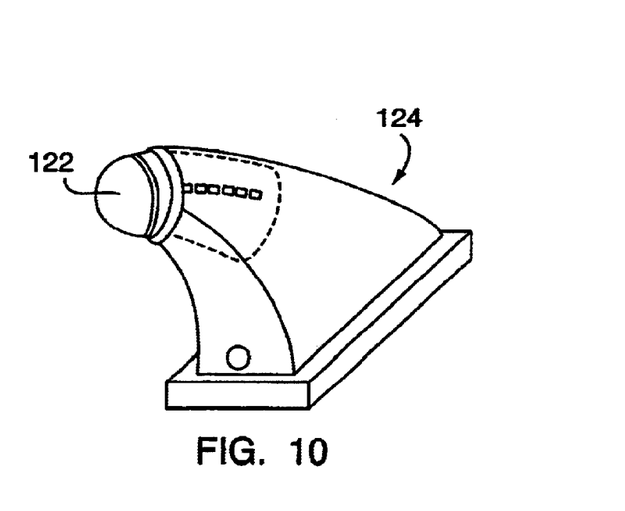
FIG. 10 is a schematic view of a massage head according to the embodiment depicted in FIG. 8.

An alternative embodiment of a myotherapy massage device 120 of the present invention is depicted in FIGS. 8, 9 and 10. In this embodiment, the massage heads 122 are positioned laterally by a base assembly 126 having two opposing bases 124 slidably engaged in a track 128 on a platform 130. Each massage head 122 is slidably engaged in each base 124 such that the massage heads 122 can be individually positioned vertically.

A method of treating myofascial pain using the myotherapy device of the present invention involves placing the device on a sturdy flat surface such as a floor, table, bed or the like. The device is positioned so that the two vibrating heads of the device come in contact with the right and left sides of the lower back as an individual lies on top of the device. The region treated is between the pelvic hip-bone (the iliac crest) and the ribs. As the individual lies down on the device, the distance between the two vibrating heads is approximately six inches.

The individual may need to make some fine adjustment to the distance between the vibrating heads so that each vibrating head comes in contact with the outer sides of the muscles that run along both sides of the spine thereby placing the point of contact on the lateral aspects of the Quadrates lumborum and erector spinae muscles on both sides of the spine. The height/elevation of the vibrating heads will need to be adjusted by the individual so that adequate pressure is applied to these muscles without causing marked discomfort. The height is adjusted by turning the knob on the side of the device. Approximately one and one half minutes of vibrating pressure are applied to the muscles. The time and amount of pressure being applied may be altered based upon therapeutic benefits.

Although the present embodiments show lateral and vertical adjustments of the substantially parallel massage heads via mechanical adjusting devices, additional adjusting devices are contemplated by the present invention such as, but not limited to, hydraulics, electrical and/or electronics to provide any or all of the operating and adjustment functions herein. In other words, automatic apparatuses may be provided to turn a crank to lift the lift arm or to adjust the device laterally. It is to be understood that the present invention is not limited to the embodiments described above, but encompasses any and all embodiments within the scope of the following claims.

What is claimed is:

1. A myotherapy massage device for the treatment of lower back myofascial pains, the device comprising:
   two laterally spaced massage heads, with each massage head having vibration means;
   a means for positioning the massage heads vertically relative to one another;
   a means for positioning the massage heads laterally relative to one another;
   wherein each massage head has a motor housing enclosing the vibration means, wherein the motor housing comprises:
   a tube having a bottom end, and a top end;
   a bottom cap disposed on the bottom end;
   a top cap disposed on the top end opposite the bottom cap; and
   wherein the vibration means is disposed within the motor housing; and
   the massage device further comprising a retention plate disposed between the top and bottom ends of the tube wherein the top cap contacts and rests upon the retention plate, thereby creating top and bottom spaces within the motor housing such that the top space adjacent the top cap is smaller than the bottom space adjacent the bottom cap.

2. A myotherapy massage device for the treatment of lower back myofascial pains, the device comprising:
- two laterally spaced massage heads, with each massage head having vibration means;
- a means for positioning the massage heads vertically relative to one another;
- a means for positioning the massage heads laterally relative to one another;
- wherein each massage head has a motor housing enclosing the vibration means,
- wherein the motor housing comprises:
  - a tube having a bottom end, and a top end;
  - a bottom cap disposed on the bottom end;
  - a top cap disposed on the top end opposite the bottom cap; and
  - wherein the vibration means is disposed within the motor housing;
- the device further comprising a retention plate disposed between the top and bottom ends of the tube wherein the top cap contacts and rests upon the retention plate, thereby creating top and bottom spaces within the motor housing such that the top space adjacent the top cap is smaller than the bottom space adjacent the bottom cap; and
- wherein the vibration means comprises a motor which turns an asymmetric weight thereby producing vibration.

3. A myotherapy massage device for the treatment of lower back myofascial pains, the device comprising:
- two laterally spaced massage heads, with each massage head having vibration means;
- a means for positioning the massage heads vertically relative to one another;
- a means for positioning the massage heads laterally relative to one another;
- wherein each massage head has a motor housing enclosing the vibration means,
- wherein the motor housing comprises:
  - a tube having a bottom end, and a top end;
  - a bottom cap disposed on the bottom end;
  - a top cap disposed on the top end opposite the bottom cap;
  - wherein the vibration means is disposed within the motor housing;
- the device further comprising a retention plate disposed between the top and bottom ends of the tube wherein the top cap contacts and rests upon the retention plate, thereby creating top and bottom spaces within the motor housing such that the top space adjacent the top cap is smaller than the bottom space adjacent the bottom cap;
- wherein the vibration means comprises a motor which turns an asymmetric weight thereby producing vibration; and
- wherein the motor is disposed in the bottom space and attached to the retention plate and the weight is permitted free movement in the top space.

4. A myotherapy massage device for the treatment of lower back myofascial pains, the device comprising:
- two laterally spaced massage heads, with each massage head having vibration means;
- a means for positioning the massage heads vertically relative to one another;
- a means for positioning the massage heads laterally relative to one another;
- wherein each massage head has a motor housing enclosing the vibration means,
- wherein the motor housing comprises:
  - a tube having a bottom end, and a top end;
  - a bottom cap disposed on the bottom end;
  - a top cap disposed on the top end opposite the bottom cap;
  - wherein the vibration means is disposed within the motor housing; and
- said massage device further comprising a coil compression spring disposed in the motor housing between the bottom cap and the top cap thereby cushioning the vibration means such that the vibration of the massage head is dampened with respect to the motor housing and amplified with respect to the top cap.

5. A myotherapy massage device for the treatment of lower back myofascial pains, the device comprising:
- two laterally spaced massage heads, with each massage head having vibration means;
- a means for positioning the massage heads vertically relative to one another;
- a means for positioning the massage heads laterally relative to one another;
- wherein each massage head has a motor housing enclosing the vibration means,
- wherein the motor housing comprises:
- a tube having a bottom end, and a top end;
- a bottom cap disposed on the bottom end;
- a top cap disposed on the top end opposite the bottom cap; and
- wherein the vibration means is disposed within the motor housing;
- the massage device further comprising a retention plate disposed between the top and bottom ends of the tube wherein the top cap contacts and rests upon the retention plate, thereby creating top and bottom spaces within the motor housing such that the top space adjacent the top cap is smaller than the bottom space adjacent the bottom cap; and
- said massage device further comprising a coil compression spring disposed in the motor housing between the bottom cap and the retention plate thereby cushioning the vibration means such that the vibration of the massage head is dampened with respect to the motor housing.

6. A myotherapy massage device for the treatment of lower back myofascial pains, the device comprising:
- two laterally spaced massage heads, with each massage head having vibration means;
- a means for positioning the massage heads vertically relative to one another;
- a means for positioning the massage heads laterally relative to one another;
- wherein each massage head has a motor housing enclosing the vibration means, wherein the motor housing comprises:
- a tube having a bottom end, and a top end;
- a bottom cap disposed on the bottom end;
- a top cap disposed on the top end opposite the bottom cap;
- wherein the vibration means is disposed within the motor housing; and
- said massage device further comprising an edge circumnavigating the tube adjacent the bottom end of the tube such that some length of tube extends therebelow.

7. A myotherapy massage device for the treatment of lower back myofascial pains, the device comprising:
  two laterally spaced massage heads, with each massage head having vibration means;
  a means for positioning the massage heads vertically relative to one another;
  a means for positioning the massage heads laterally relative to one another;
  wherein the means for positioning the massage heads laterally relative to one another comprises an apparatus having two opposing base assemblies slidably connected to each other by two guide rods, wherein each base assembly comprises two opposing bases having the means for positioning the massage heads vertically relative to one another disposed between the bases, and a guide disposed on each base having a first opening therethrough for slidably receiving a guide rod.

8. A myotherapy massage device for the treatment of lower back myofascial pains, the device comprising:
  two laterally spaced massage heads, with each massage head having vibration means;
  a means for positioning the massage heads vertically relative to one another;
  a means for positioning the massage heads laterally relative to one another;
  wherein the means for positioning the massage heads laterally relative to one another comprises an apparatus having two opposing base assemblies slidably connected to each other by two guide rods, wherein each base assembly comprises two opposing bases having the means for positioning the massage heads vertically relative to one another disposed between the bases, and a guide disposed on each base having a first opening therethrough for slidably receiving a guide rod; and
  said massage device further comprising means for restricting the movement of the base assemblies relative to the guide rods.

9. A myotherapy massage device for the treatment of lower back myofascial pains, the device comprising:
  two laterally spaced massage heads, with each massage head having vibration means;
  a means for positioning the massage heads vertically relative to one another;
  a means for positioning the massage heads laterally relative to one another;
  wherein the means for positioning the massage heads laterally relative to one another comprises an apparatus having two opposing base assemblies slidably connected to each other by two guide rods, wherein each base assembly comprises two opposing bases having the means for positioning the massage heads vertically relative to one another disposed between the bases, and a guide disposed on each base having a first opening therethrough for slidably receiving a guide rod; and
  wherein each guide further comprises a perpendicular threaded second opening, bisecting the first opening, for receiving a knob having a screw extension thereon which can be tightened to secure the guide rod in place.

10. A myotherapy massage device for the treatment of lower back myofascial pains, the device comprising:
  two laterally spaced massage heads, with each massage head having vibration means;
  a means for positioning the massage heads vertically relative to one another;
  a means for positioning the massage heads laterally relative to one another;
  wherein the means for positioning each massage head vertically comprises:
  a base assembly composed of two opposing bases and a lift arm disposed between the two opposing bases;
  the lift arm has a length with a first and second end,
  a means for attaching a massage head at the first end
  a pivot axis at the second end thereof, and
  a lift axis disposed between the first and second ends of the lift arm;
  a linker, having first and second ends, with the first end of the linker pivotably disposed on the lift axis and the second end of the linker pivotably disposed between the two opposing bases;
  a pivot axis assembly having a first threaded opening therein forming a passage therethrough for receiving a crankshaft therethrough and a second threaded opening forming a means for receiving the pivot axis of the second end of the lift arm;
  the crank shaft having a length, a first end, and a second end;
  a first spacer block attached to and disposed between the two opposing bases and having a threaded opening for receiving a first end of the crank shaft therethrough; and
  a second spacer block attached to and disposed between the two opposing bases and having a threaded opening therein for receiving a second end of the crankshaft.

11. A myotherapy massage device for the treatment of lower back myofascial pains, the device comprising:
  two laterally spaced massage heads, with each massage head having vibration means;
  a means for positioning the massage heads vertically relative to one another;
  a means for positioning the massage heads laterally relative to one another;
  wherein the means for positioning each massage head vertically comprises:
  a base assembly composed of two opposing bases and a lift arm disposed between the two opposing bases;
  the lift arm has a length with a first and second end,
  a means for attaching a massage head at the first end
  a pivot axis at the second end thereof, and
  a lift axis disposed between the first and second ends of the lift arm;
  a linker, having first and second ends, with the first end of the linker pivotably disposed on the lift axis and the second end of the linker pivotably disposed between the two opposing bases;
  a pivot axis assembly having a first threaded opening therein forming a passage therethrough for receiving a crankshaft therethrough and a second threaded opening forming a means for receiving the pivot axis of the second end of the lift arm;
  the crank shaft having a length, a first end, and a second end;
  a first spacer block attached to and disposed between the two opposing bases and having a threaded opening for receiving a first end of the crank shaft therethrough; and
  a second spacer block attached to and disposed between the two opposing bases and having a threaded opening therein for receiving a second end of the crankshaft; and wherein the crankshaft has a means for rotating the crankshaft disposed on the first end of the crankshaft.

12. A myotherapy massage device for the treatment of lower back myofascial pains, the device comprising:

two laterally spaced massage heads, with each massage head having vibration means;

a means for positioning the massage heads vertically relative to one another;

a means for positioning the massage heads laterally relative to one another;

wherein the means for positioning each massage head vertically comprises:

a base assembly composed of two opposing bases and a lift arm disposed between the two opposing bases;

the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm; the crank shaft having a length, a first end, and a second end;

a first spacer block attached to and disposed between the two opposing bases and having a threaded opening for receiving a first end of the crank shaft therethrough;

a second spacer block attached to and disposed between the two opposing bases and having a threaded opening therein for receiving a second end of the crankshaft; and said massage device further comprising a bend in the lift arm.

13. A myotherapy massage device for the treatment of lower back myofascial pains, the device comprising:

two laterally spaced massage heads, with each massage head having vibration means;

a means for positioning the massage heads vertically relative to one another;

a means for positioning the massage heads laterally relative to one another;

wherein the means for positioning each massage head vertically comprises:

a base assembly composed of two opposing bases and a lift arm disposed between the two opposing bases;

the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crank shaft having a length, a first end, and a second end;

a first spacer block attached to and disposed between the two opposing bases and having a threaded opening for receiving a first end of the crank shaft therethrough;

a second spacer block attached to and disposed between the two opposing bases and having a threaded opening therein for receiving a second end of the crankshaft; and wherein the second end of the lift arm comprises a U-shaped extension such that the pivot axis assembly fits between two legs of the U-shaped extension.

14. A myotherapy massage device for the treatment of lower back myofascial pains, the device comprising:

two laterally spaced massage heads, with each massage head having vibration means;

a means for positioning the massage heads vertically relative to one another;

a means for positioning the massage heads laterally relative to one another;

wherein the means for positioning each massage head vertically comprises:

a base assembly composed of two opposing bases and a lift arm disposed between the two opposing bases;

the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crank shaft having a length, a first end, and a second end;

a first spacer block attached to and disposed between the two opposing bases and having a threaded opening for receiving a first end of the crank shaft therethrough;

a second spacer block attached to and disposed between the two opposing bases and having a threaded opening therein for receiving a second end of the crankshaft;

wherein the second end of the lift arm comprises a U-shaped extension such that the pivot axis assembly fits between two legs of the U-shaped extension; and wherein the two legs of the U-shaped extension extend past the pivot axis.

15. A myotherapy massage device for the treatment of lower back myofascial pains, the device comprising:

two laterally spaced massage heads, wherein each massage head has a motor housing enclosing a vibration means, the motor housing has a tube having bottom and top ends, a bottom cap disposed on the bottom end of the motor housing, and a top cap disposed on the top end of the motor housing opposite the bottom cap;

a means for positioning the massage heads vertically relative to one another;

a means for positioning the massage heads laterally relative to one another;

wherein the means for positioning the massage heads laterally comprises an apparatus having two opposing base assemblies slidably connected to one another by two guide rods, wherein each base assembly comprises two opposing bases having the means for positioning the massage heads vertically disposed between the bases, and a guide disposed on each base having a first opening therethrough for slidably receiving a guide rod.

16. A myotherapy massage device for the treatment of lower back myofascial pains, the device comprising:

two laterally spaced massage heads, wherein each massage head has a motor housing enclosing a vibration means, the motor housing has a tube having bottom and top ends, a bottom cap disposed on the bottom end of the motor housing, and a top cap disposed on the top end of the motor housing opposite the bottom cap;

a means for positioning the massage heads vertically relative to one another;

a means for positioning the massage heads laterally relative to one another;

wherein the means for positioning the massage heads laterally comprises an apparatus having two opposing base assemblies slidably connected to one another by two guide rods, wherein each base assembly comprises two opposing bases having the means for positioning the massage heads vertically disposed between the bases, and a guide disposed on each base having a first opening therethrough for slidably receiving a guide rod; and wherein the means for positioning each massage head vertically comprises:

a base assembly composed of two opposing bases and a lift arm disposed between the two opposing bases;

the lift arm has a length with a first and second end,
a means for attaching a massage head at the first end
a pivot axis at the second end thereof, and
a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crankshaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft.

17. A myotherapy massage device for the treatment of lower back myofascial pains, the device comprising:

two laterally spaced massage heads, wherein each massage head has a motor housing enclosing a vibration means, the motor housing has a tube having bottom and top ends, a bottom cap disposed on the bottom end of the motor housing, and a top cap disposed on the top end of the motor housing opposite the bottom cap;

a means for positioning the massage heads vertically relative to one another;

a means for positioning the massage heads laterally relative to one another;

wherein the means for positioning the massage heads laterally comprises an apparatus having two opposing base assemblies slidably connected to one another by two guide rods, wherein each base assembly comprises two opposing bases having the means for positioning the massage heads vertically disposed between the bases, and a guide disposed on each base having a first opening therethrough for slidably receiving a guide rod;

wherein the means for positioning each massage head vertically comprises:

a base assembly composed of two opposing bases and a lift arm disposed between the two opposing bases;

the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crankshaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft; and wherein the means for attaching the massage head to the first end of the lift arm comprises an opening therethrough for receiving the motor housing of the massage head.

18. A myotherapy massage device for the treatment of lower back myofascial pains, the device comprising:

two laterally spaced massage heads, wherein each massage head has a motor housing enclosing a vibration means, the motor housing has a tube having bottom and top ends, a bottom cap disposed on the bottom end of the motor housing, and a top cap disposed on the top end of the motor housing opposite the bottom cap;

a means for positioning the massage heads vertically relative to one another;

a means for positioning the massage heads laterally relative to one another;

wherein the means for positioning the massage heads laterally comprises an apparatus having two opposing base assemblies slidably connected to one another by two guide rods, wherein each base assembly comprises two opposing bases having the means for positioning the massage heads vertically disposed between the bases, and a guide disposed on each base having a first opening therethrough for slidably receiving a guide rod;

wherein the means for positioning each massage head vertically comprises:

a base assembly composed of two opposing bases and a lift arm disposed between the two opposing bases;

the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crankshaft having a length, a first end, and a second end;

a first spacer block attached to and disposed between the two opposing bases and having a threaded opening for receiving a first end of the crank shaft therethrough;

a second spacer block attached to and disposed between the two opposing bases and having a threaded opening therein for receiving a second end of the crankshaft; and wherein the crankshaft has a handle for rotating the shaft disposed on the first end of the shaft.

19. A myotherapy massage device for the treatment of lower back myofascial pains, the device comprising:

two laterally spaced massage heads, wherein each massage head has a motor housing enclosing a vibration means, the motor housing has a tube having bottom and top ends, a bottom cap disposed on the bottom end of the motor housing, and a top cap disposed on the top end of the motor housing opposite the bottom cap;

a means for positioning the massage heads vertically relative to one another;

a means for positioning the massage heads laterally relative to one another;

wherein the means for positioning the massage heads laterally comprises an apparatus having two opposing base assemblies slidably connected to one another by two guide rods, wherein each base assembly comprises two opposing bases having the means for positioning the massage heads vertically disposed between the bases, and a guide disposed on each base having a first opening therethrough for slidably receiving a guide rod;

wherein the means for positioning each massage head vertically comprises:

a base assembly composed of two opposing bases and a lift arm disposed between the two opposing bases;

the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crankshaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft;

wherein the means for attaching the massage head to the first end of the lift arm comprises an opening therethrough for receiving the motor housing of the massage head; and said massage device further comprising a bend in the lift arm at the lift axis.

20. A massage device comprising:

a massage head having a motor housing enclosing a vibration means, the motor housing has a tube having bottom and top ends, a bottom cap disposed on the bottom end of the motor housing, and a top cap disposed on the top end of the motor housing opposite the bottom cap; and a means for positioning each massage head vertically comprising a base assembly composed of two opposing bases and a lift arm disposed between the two opposing bases; the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crank shaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft.

21. A massage device comprising:

a massage head having a motor housing enclosing a vibration means, the motor housing has a tube having bottom and top ends, a bottom cap disposed on the bottom end of the motor housing, and a top cap disposed on the top end of the motor housing opposite the bottom cap; and a means for positioning each massage head vertically comprising a base assembly composed of two opposing bases and a lift arm disposed between the two opposing bases; the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crank shaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft; and wherein the means for attaching the massage head to the first end of the lift arm comprises an opening therethrough for receiving the motor housing of the massage head.

22. A massage device comprising:

a massage head having a motor housing enclosing a vibration means, the motor housing has a tube having bottom and top ends, a bottom cap disposed on the bottom end of the motor housing, and a top cap disposed on the top end of the motor housing opposite the bottom cap; and a means for positioning each massage head vertically comprising a base assembly composed of two opposing bases and a lift arm disposed between the two opposing bases; the lift arm has a length with a first and second end, a means for attaching a massage head at the first end a pivot axis at the second end thereof, and a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crank shaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft; and wherein the crankshaft has a handle for rotating the shaft disposed on the first end of the shaft.

23. A massage device comprising:

a massage head having a motor housing enclosing a vibration means, the motor housing has a tube having bottom and top ends, a bottom cap disposed on the bottom end of the motor housing, and a top cap disposed on the top end of the motor housing opposite the bottom cap; and a means for positioning each massage head vertically comprising a base assembly composed of two opposing bases and a lift arm disposed between the two opposing bases; the lift arm has a length with a first and second end, a means for attaching a massage head at the first end a pivot axis at the second end thereof;

a lift axis disposed between the first and second ends of the lift arm;

a linker, having first and second ends, with the first end of the linker pivotably disposed on the lift axis and the second end of the linker pivotably disposed between the two opposing bases;

a pivot axis assembly having a first threaded opening therein forming a passage therethrough for receiving a crankshaft therethrough and a second threaded opening forming a means for receiving the pivot axis of the second end of the lift arm;

the crank shaft having a length, a first end, and a second end;

a first spacer block attached to and disposed between the two opposing bases and having a threaded opening for receiving a first end of the crank shaft therethrough; and a second spacer block attached to and disposed between the two opposing bases and having a threaded opening therein for receiving a second end of the crankshaft; and further comprising a bend in the lift arm at the lift axis.

* * * * *